United States Patent [19]

Domingues

[11] Patent Number: 5,650,183
[45] Date of Patent: Jul. 22, 1997

[54] PREPARATION OF REFRIGERATABLE DOUGH PRODUCTS CONTAINING *SACCHAROMYCES CEREVISIAE* ATCC 74212

[75] Inventor: David J. Domingues, Plymouth, Minn.

[73] Assignee: The Pillsbury Company, Minneapolis, Minn.

[21] Appl. No.: 521,130

[22] Filed: Aug. 29, 1995

Related U.S. Application Data

[60] Continuation of Ser. No. 277,901, Jul. 28, 1994, abandoned, which is a division of Ser. No. 26,927, Mar. 5, 1993, abandoned, which is a continuation-in-part of Ser. No. 732,081, Jul. 18, 1991, abandoned.

[51] Int. Cl.$^6$ .................... A21D 8/00; C12N 1/18
[52] U.S. Cl. .................... 426/19; 426/8; 426/21; 426/62; 435/254.21; 435/255.2; 435/942
[58] Field of Search ............... 435/255.2, 254.21, 435/942; 426/8, 19, 21, 62

[56] References Cited

PUBLICATIONS

Lobo, et al., Archives of Biochemistry and Biophysics, vol. 182, 1977, pp. 639–645.

*Primary Examiner*—David M. Naff
*Attorney, Agent, or Firm*—Janal M. Kalis; Aleya Rahman

[57] ABSTRACT

Refrigeratable yeast-leavened dough products are prepared that can be stored for extended periods of time at refrigeration temperatures. The dough composition and yeast strain are chosen to limit the total leavening action of the yeast by controlling the mount of substrate in the dough fermentable by the yeast. Dough compositions made in accordance with the invention are capable of being leavened at elevated temperatures, yet stored in a sealed container at refrigeration temperatures for extended periods of time. In one embodiment, a maltose negative yeast is used and sucrose or the like is added to the dough to serve as a fermentable substrate for the dough; this dough is suitable for storage times of up to 30 days or so. In a particularly useful embodiment which is suitable for even longer storage at refrigeration temperatures, the yeast used in the dough is substantially incapable of fermenting carbohydrates native to the dough and a predetermined quantity of a non-native carbohydrate fermentable by the yeast (e.g. galactose) is added to the dough to provide the desired mount of proofing. A preferred yeast strain for this embodiment is *Saccharomyces cerevisiae* ATCC 74212.

1 Claim, 10 Drawing Sheets

PREPARATION OF REFRIGERATABLE DOUGH PRODUCTS CONTAINING *SACCHAROMYCES CEREVISIAE* ATCC 74212

This is a continuation of prior application Ser. No. 08/277,901 filed Jul. 20, 1994, now abandoned, which is a divisional of application Ser. No. 08/026,927 filed on Mar. 5, 1993, now abandoned, which is a continuation-in-part of application Ser. No. 07/732,081, now abandoned.

FIELD OF THE INVENTION

The present invention relates to refrigeratable dough products for use in making edible baked goods. In particular, the invention provides a yeast-leavened dough which can be stored for extended periods of time at refrigeration temperatures.

BACKGROUND OF THE INVENTION

A wide range of refrigeratable dough products are currently available to consumers for producing numerous different baked products. These refrigerated doughs range from doughs for biscuits and breads to sweet rolls to cornbread products. These dough products are rather popular with consumers because they are very convenient and easy to use. Most of these products are sold in a pre-proofed state so that they can be opened to remove the dough and the dough can be baked immediately. Packaging and selling doughs in a pre-proofed state omits any necessity on the part of the consumers to carefully proof the dough for an extended period of time before baking it.

In producing refrigeratable dough products, suitably sized portions of unproofed dough are placed in individual containers. The dough is then proofed within the container, such as by holding the dough at an elevated temperature, causing the dough to expand. The dough will continue to proof until a positive internal pressure of about 15–20 psi is attained; most such containers will rupture or explode if the internal pressure of the container substantially exceeds about 40 psi. Such products are desirably capable of storage at refrigeration temperatures for at least a couple of weeks, and desirably as long as a few months, without any significant degradation of the quality of the dough or any substantial likelihood of having the containers rupture.

One disadvantage of refrigeratable dough products on the market today is that these doughs generally cannot be leavened with yeast. When yeast is used in a dough, the yeast cells will tend to continue to grow, or at least continue metabolization, even at refrigeration temperatures. The yeast therefore continues to produce carbon dioxide over the entire storage time, unless the dough is stored in a frozen state. Although allowing yeast to ferment for the entire shelf life of the dough may work if the dough is intended to be used immediately, extended storage (e.g. about two weeks or more) in a sealed container generally will not work because the pressure in the container will quickly build and rapture the container. If a conventional yeast-leavened dough were placed in a standard dough product container, the container may be expected to fail in no more than about two days. Additionally, continued activity of the yeast beyond the desired degree of proofing can deleteriously affect the organoleptic and theological properties of the dough, producing unacceptable final baked products.

To date, manufacturers of refrigeratable doughs have had to replace yeast with chemical leavening agents, such as baking soda or the like. Such chemical leavening agents generally comprise a combination of a leavening acid and a leavening base, with the acid and base portions reacting to generate carbon dioxide, causing the dough to rise. One of the primary advantages of such leavening agents is that their behavior is based upon a predictable chemical reaction, permitting one to readily control the volume of carbon dioxide produced to leaven the dough. Once the chemical reaction of the leavening agents has proceeded to completion, carbon dioxide production ceases.

Although a chemically leavened dough product can be stored for extended periods of time at refrigeration temperatures, the final baked product obtained by baking such a dough is noticeably inferior to a product made with a yeast-leavened dough. Products made from yeast-leavened doughs are widely acknowledged to have superior taste, aroma and texture than those made with chemical leavening agents. Commercial dough manufacturers frequently add ingredients for the sole purpose of simulating yeast-leavened doughs. For instance, these manufacturers frequently add yeast flavoring, such as inactive pasteurized yeast cultures, to the chemically leavened dough. Even with such additives, baked products made from chemically leavened doughs lack the characteristic flavor and aroma of yeast-leavened dough and continue to exhibit relatively poor texture.

Others have attempted to solve the problems associated with storage of yeast-leavened doughs by storing the doughs at freezing temperatures rather than refrigeration temperatures. Frozen yeast-leavened doughs can yield baked goods which are noticeably better than chemically leavened refrigerated doughs. Yeast becomes inactive when frozen, thereby avoiding the problems associated with continued carbon dioxide evolution at refrigeration temperatures.

In a published European patent application (Published European Patent 0 442 575, published Aug. 21, 1991), Gist-Brocades describes a dough composition which uses a substrate limitation concept. In accordance with this disclosure, a dough is leavened with a maltose negative yeast (a yeast which cannot ferment maltose) and the dough is frozen. Gist-Brocades states that the dough may be thawed, proofed and baked anytime the same day without having to carefully monitor the proofing time. However, this dough is not designed by Gist-Brocades to be stored at refrigeration temperatures for extended periods of time, e.g. two weeks or more.

However, frozen doughs simply are not as convenient as pre-proofed refrigerated dough products. Whereas such refrigerated doughs can be baked immediately after removal from the container, frozen doughs must be allowed to thaw prior to baking. Also, since proofed dough does not survive freezing very well, frozen doughs generally must be proofed after thawing and prior to baking. This can further delay the baking of the dough. The consumer must spend more time monitoring the proofing process to avoid over-proofing the dough, making sure to place the dough in the oven for baking at the right time. Not only do such frozen doughs require more attention than do refrigerated dough products, it also requires the consumer to plan well in advance so the dough can be thawed and proofed to provide the baked goods at the desired time.

Hence, there has been a long-felt need in the industry for a yeast-leavened dough that can be stored at refrigeration temperatures for extended periods of time. To date, though, commercial producers have been unable to make and sell refrigeratable yeast-leavened doughs suitable for large-scale commercial production and extended shelf life, despite the obvious economic potential of such a product. It appears that the problems associated with the continued generation of carbon dioxide by the yeast have precluded any such product.

SUMMARY OF THE INVENTION

The present invention provides a method of making refrigeratable yeast-containing doughs and dough products made therewith. In another aspect, the invention provides a yeast-leavened refrigeratable dough composition, a dough product comprising refrigeratable dough in a container, and a baked product made from such refrigeratable dough. In accordance with the invention, a preselected strain of yeast is mixed with flour and water and, perhaps, other ingredients to form a dough. The yeast and the dough composition are chosen so that the total amount of carbohydrate or carbohydrates fermentable by the yeast in the dough is limited.

In one preferred embodiment, the yeast is substantially incapable of fermenting carbohydrates native to the flour used in the dough and a non-native carbohydrate, such as galactose, is added to the dough in an amount selected to provide the desired volume of carbon dioxide. By so doing, one may limit the maximum volume of carbon dioxide which the yeast can generate. This, in turn, prevents generation of sufficient carbon dioxide to rupture a sealed container of dough, even if the temperature of the dough is inadvertently elevated.

The method may also include the additional steps of placing the resultant dough in a pressurizable container and heating the dough within the container to an elevated temperature for proofing. Once the dough in the container has been proofed, the temperature of the dough within the container is reduced to refrigeration temperatures and the dough is stored at refrigeration temperatures for an extended period of time. A method of this embodiment may further comprise the step of removing the dough from the container and baking it to produce a baked good.

DETAILED DESCRIPTION OF THE PREFERRED EMBODIMENTS

In accordance with the present invention, a dough product is prepared wherein the dough composition and the yeast used therein are chosen in a manner that effectively and controllably limits the leavening action of the yeast by controlling the amount of substrate fermentable by the yeast in the dough. Strains of yeast which do not ferment certain carbohydrates are known in the art; often, two different strains of the same species of yeast are unable to ferment the same sugars. Therefore, a strain of yeast may be utilized in a dough composition which is capable of fermenting only selected sugars. By controlling the total amount of those sugars in the dough composition, the amount of fermentation can be controlled.

As explained above, even at refrigeration temperatures, most yeast will generate carbon dioxide. If the sugar substrate fermentable by the yeast is limited, carbon dioxide generation will substantially cease when the sugar is exhausted. Hence, by either allowing the yeast to metabolize the fermentable sugars in the dough for a given period of time prior to canning or controlling the sugar content of the dough, carbon dioxide generation by the yeast can be substantially terminated once a certain predetermined volume has been reached, regardless of the temperature of the dough. Accordingly, the total volume of carbon dioxide generated in the container can be prevented from reaching a level sufficient to increase internal pressure and rupture the container.

Wheat flours used in most commercial dough manufacturing operations contain about 5 weight percent (wt. %) of damaged starch. Alpha- and beta-amylases (inherent in wheat flour) convert such starch into maltose, among other sugars. Maltose and some of the other sugars produced by the action of the amylase are metabolizable by many strains of yeast.

In an earlier embodiment of the invention, a strain of yeast which did not ferment maltose, referred to as "maltose negative," or just "MAL–," was chosen. Such yeast can usually ferment other types of sugars, such as sucrose or dextrose. A number of yeasts which ferment sucrose but not maltose ("SUC+/MAL–") are commercially available, including the following strains *Saccharomyces Cerevisiae:* DZ (CBS 109.90), DS 10638 (CBS 110.90), DS 16887 (CBS 111.90) V 79 (CBS 7045), and V 372 (CBS 7437). Approximately 100–200 ml of CO2 per 100 grams of dough at 32° C. is usually sufficient for proofing. The total amount of fermentable sugar in the dough was adjusted in an attempt to limit the volume of carbon dioxide gas produced by fermentation of the entire fermentable sugar supply.

EXAMPLE 1

In order to test a dough product leavened with a MAL– yeast as a means of providing a refrigeratable yeast-leavened dough composition, water and a MAL– yeast were slurried together to produce a total combined weight of approximately 194 grams. The slurry contained 189 grams of water and 4.8 grams of the yeast. The yeast used in making the slurry was a MAL– swain of yeast which was obtained in a paste form. The paste was mixed with water at room temperature (approximately 23° C.) and allowed to sit at room temperature for about 10–15 mutes.

To this slurry was added 261.74 grams of flour, 18.77 grams of wheat gluten pre-blend, 3.60 grams of salt and 1.20 grams of dextrose. The wheat gluten pre-blend was 75 wt. % vital wheat gluten, 21.9 wt. % hard, high gluten, enriched ingredient flour, 2.50 wt. % xanthan gum, and 0.616 wt. % azodicarbonamide premix. The resulting dough composition therefore contained 54.53 wt. % flour, 3.91 wt. % gluten pre-blend, 0.75 wt. % salt, and 0.25 wt. % dextrose, with a final concentration of 1.130 wt. % MAL– yeast.

The dough composition was mixed in a Farinograph™ mixing bowl at 60 rpm for 4.5 minutes. Immediately after mixing, a 50-gram sample of the dough composition was placed into a Risograph™ testing machine. The Risograph is commercially available from Sheldon Manufacturing, Inc. for detecting the volume of gas, e.g. carbon dioxide, generated by a sample and the rate at which the gas is generated.

Figure 1:
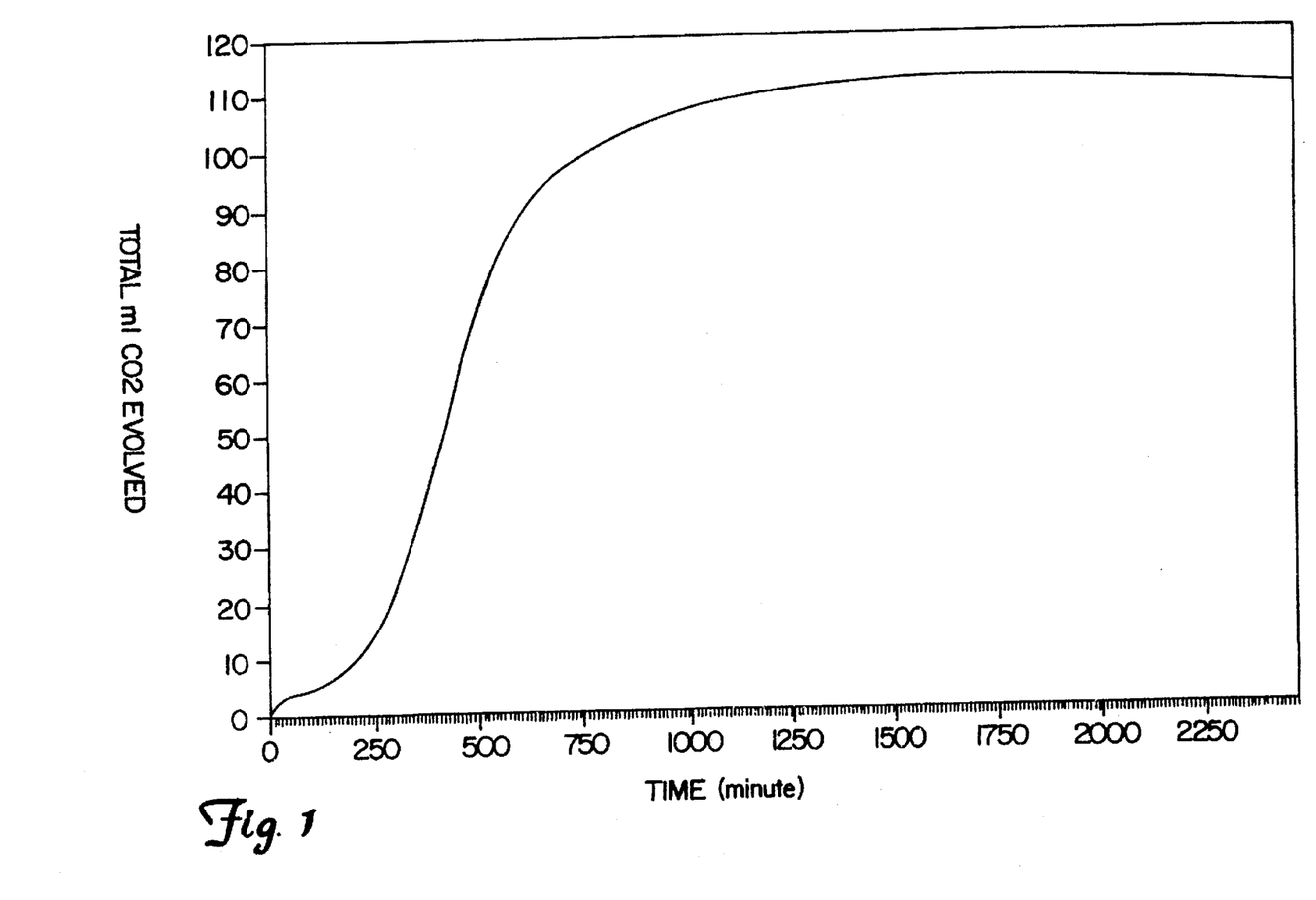
FIG. 1 is a graph showing the volume of carbon dioxide generated by MAL– yeast in a dough composition heat treated at 32° C.
Figure 2:
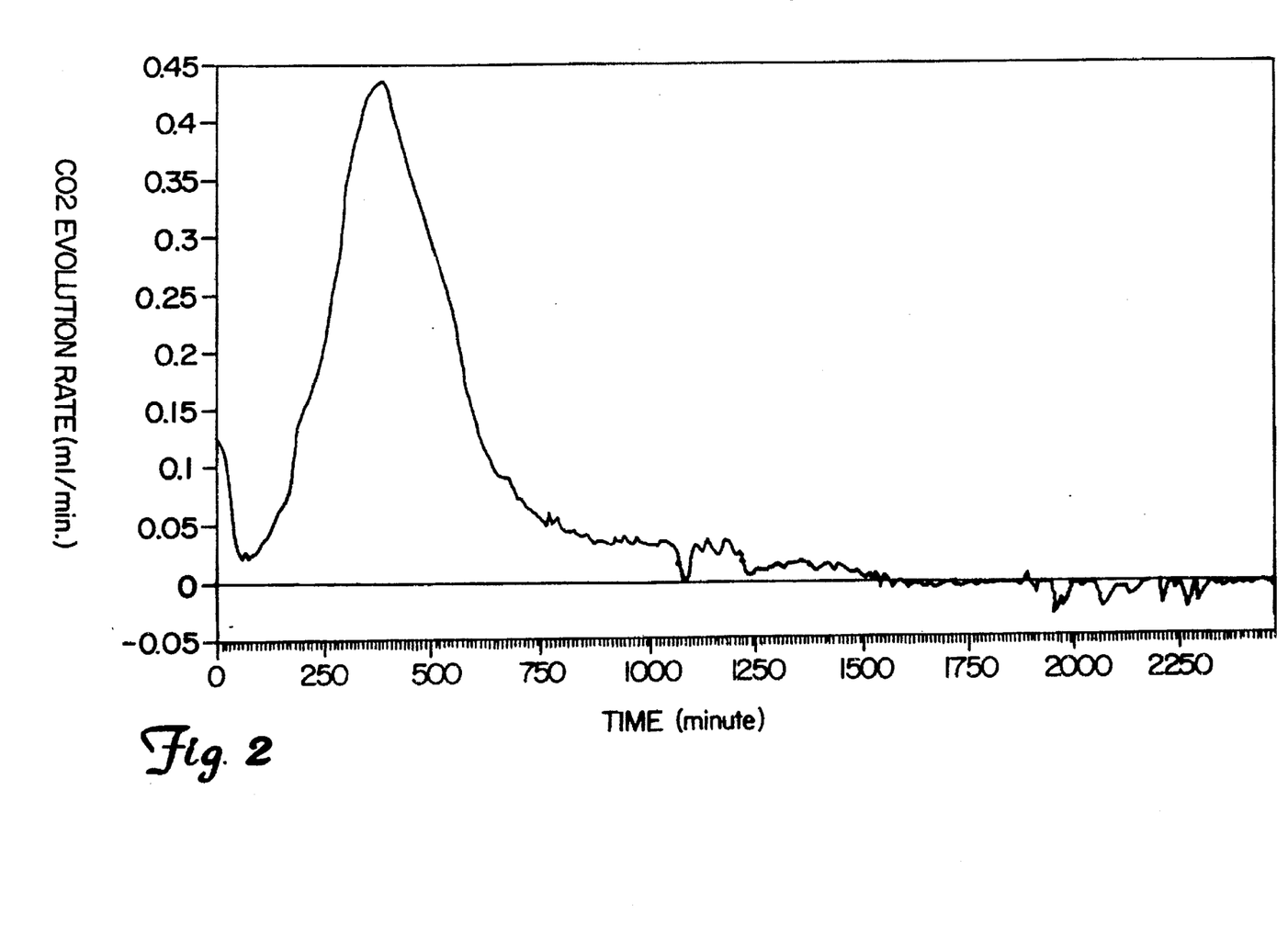
FIG. 2 shows the rate of carbon dioxide evolution for the dough shown in FIG. 1.

FIGS. 1 and 2 show the data collected in the Risograph for the sample. Of particular interest, the dough appeared to effectively cease producing carbon dioxide after about 1500 minutes at 32° C. Dough products made with this dough by placing the dough in standard spirally wound refrigeratable dough containers were found to maintain acceptable internal pressures, e.g., below about 20 psi, for about 25 days. However, carbon dioxide once again began to be generated by the dough after about 25 days. This renewed activity of the yeast in the dough was projected to be sufficient to generate enough carbon dioxide to cause all of the containers of Example 1 to rupture after about 50–55 days.

It has not been conclusively determined why the yeast became active after apparently substantially ceasing fermentation. However, one factor which is believed to have contributed to the generation of additional carbon dioxide, and subsequent failure of the containers, is a change in the carbohydrates present in the dough. As noted above, alpha- and beta-amylases, which are inherent in wheat flours, act on carbohydrates present in the dough, and particularly in the flour. Over time, these amylases break down oligosaccharides which are not fermentable by the yeast, such as maltose and maltotriose, into sugars which can be fermented by the yeast. Accordingly, it is anticipated that, even if the yeast used in such a dough composition were truly maltose negative, the changing carbohydrate profile of the dough may present sugars which are fermentable by the yeast. Accordingly, the dough could continue to generate carbon dioxide and cause containers to rupture.

Thus, a dough product made with a MAL– yeast and a limited amount of initial maltose in the composition can be useful for storage at refrigeration temperatures for shorter periods of time, with a storage period on the order of about 30 days or less. If such dough products were stored for significantly longer periods of time, it is likely that the containers would begin to fail. Although a shelf life of 30 days may be suitable for some applications, current refrigerated dough products are expected to have an anticipated shelf life at refrigeration temperatures of 90 days or more. Accordingly, this MAL– embodiment of the invention may have only limited commercial application, with commercial use being limited to institutional markets, such as in-store bakeries and the like, where an anticipated shelf life of 30 days may nonetheless be considered acceptable.

In accordance with a preferred embodiment of the present invention suitable for significantly longer storage at refrigeration temperatures, the strain (or strains) of yeast used in the dough are substantially incapable of fermenting carbohydrates which are native to the flour. In the ease of doughs using wheat flour, these native carbohydrates include sugars such as maltose, sucrose, glucose, fructose and various oligosaccharides made up of these sugars. If other flours were to be used, of course, there may be some variation in the sugars native to such a flour.

Use of such a yeast has been found to effectively prevent the yeast from fermenting any carbohydrates in the dough which are either initially present in the dough composition or result from the action of alpha- and beta-amylases on the carbohydrates initially present in the dough. A predetermined quantity of a non-native carbohydrate which is fermentable by the yeast may be added to the dough to provide the desired amount of proofing. Once that substrate is consumed, the fermentation activity of the yeast appears to substantially cease, preventing further carbon dioxide generation and avoiding overfermentation of the dough. It has been found that dough compositions in accordance with this embodiment of the invention can be used to make dough products which can be stored for periods of time in excess of 90 days without rupturing or exploding.

The non-native carbohydrate which can be fermented by the yeast strain in the present dough can be virtually any carbohydrate which does not naturally occur in the flour. This carbohydrate is preferably a sugar or an oligosaccharide, though. For instance, the fermentable, non-native sugar may be galactose or lactose, a disaccharide of glucose and galactose.

In one particularly preferred embodiment, the yeast is capable of fermenting galactose, which is not native to wheat flours, but is substantially unable to ferment any sugars which are native to wheat flour; this yeast is referred to below as a "galactose positive" or "GAL+" yeast. This GAL+ yeast is mixed with flour, water and galactose to form a dough. The mount of galactose in the dough is selected to limit the activity of the yeast so that the dough is proofed no more than the desired degree. As noted above, in most circumstances about 100–200 ml of carbon dioxide per 100 grams of dough at 32° C. is sufficient to proof the dough. Accordingly, the weight to percentage of galactose in the dough composition should be chosen to generate no more than approximately 200 ml of carbon dioxide per 100 grams of dough at 32° C. The mount of galactose necessary to generate this volume of carbon dioxide will have to be determined on a case-by-case basis as the mount may vary for different strains of yeast.

Given the present disclosure, it will be well within the ability of those skilled in the art to make yeasts which are substantially incapable of fermenting carbohydrates native to flour but capable of fermenting other carbohydrates. Such yeasts can be made through standard methods of crossing yeast strains, isolating suitable strains having the desired properties and the like. These types of common techniques are described, for example, by Sherman et al. in *Methods in Yeast Genetics*, the teachings of which are incorporated herein by reference. Of particular interest in the Sherman et al. is Section III, entitled "Making Mutants", which appears on pages 273–369 of this reference Lobo and Maitra teach a method of rendering the hexokinase negative strain described above glucokinase negative (i.e., a method for making a GAL+ yeast strain) using standard techniques in "Physiological Role of Glucose-Phosphorylating Enzymes in *Saccharomyces cerevisiae*," Archives of Biochemistry and Biophysics 182, 639–645 (1977), the teachings of which are incorporated herein by reference. In accordance with that method, the hexokinase negative strain was mutagenized with N-methyl-N'-nitro-N-nitrosoguanidine in yeast extract-peptone medium (YEP) containing 50 mM glucose-free galactose, and a glucokinase-negative mutant was isolated by replica plating from a YEP galactose plate to a YEP glucose plate as a glucose-negative colony. The genotype of the mutant, determined by independent genetic analysis, was hxk1 hxk2 glk1, where hxk1 and hxk2 stand for genes coding P1 and P2 hexokinases respectively, and glk1 for the genetic determinant for glucokinase synthesis.

Although Lobo and Maitra teach one suitable method of making a yeast for use in accordance with the present invention, others methods will be apparent to those of skilled in the art. Those in the art will also realize that other strains of yeast which are substantially incapable of fermenting carbohydrates native to a particular flour but capable of fermenting non-native carbohydrates other than galactose can be made by known methods.

EXAMPLE 2

In order to test the ability of a GAL+ yeast to ferment carbohydrates which are native to a common dough system, a dough composition containing GAL+ yeast was prepared. This dough formula included 870.75 g (58.05 wt. %) wheat flour, 529.80 g (35.32 wt. %), water, 58.20 g (3.88 wt. %) of the wheat gluten preblend used in Example 1, 11.25 g (0.75 wt. %) salt and 28.50 (2.00 wt. %) yeast. The yeast used in this experiment was a GAL+ strain of *Saccharomyces Cerevisiae* designated as D308.3; this yeast was of the genotype αhxk1 hxk2 glk1 ade1 trp1 his2 met4. This yeast is available to the public from the Yeast Genetic Stock Center at the Donner Laboratory in the Department of Molecular and Cell Biology of the University of California, Berkley (YGSC); in the Seventh Edition of the catalog of the YGSC dated Mar. 15, 1991, this strain of yeast was listed under stock no. D308.3. This yeast strain was also deposited with the American Type Culture Collection of 12301 Parklawn Drive, Rockville, Md. 20852, USA (ATCC), on Mar. 5, 1993, under number ATCC 74211.

Isolated colonies of the D308.3 yeast from solid galactose agar plates were used to inoculate six 50 ml culture flasks containing liquid yeast extract-peptone ("YEP") and galactose. The samples were incubated for approximately 20 hours at about 30° C. and then used to inoculate six one-liter flask samples, which also contained YEP and galactose. These 1 L flasks were incubated for about 24 hours at 30° C., followed by incubation at about 24° C. for approximately 20 hours.

This yeast was then harvested using a GSA rotor, which is commercially available from Sorval Instruments. Sample containers for use with the GSA rotor were filled so that the total weight of the sample, lid and container was about 300 g. The sample container was spun at 2500 rpm for 20 minutes, and the supernatant fluid was immediately decanted. Enough distilled water to raise the total weight of the sample, lid and container to 300 g was added to the sample container, and the container was swirled to bring the yeast pellet back into suspension. This sample container was then spun at 2500 rpm for 20 minutes again, and the supernatant fluid was again decanted.

The washed yeast paste and water were combined to form a slurry. This slurry was mixed with the other ingredients in a table-top Hobart mixer. The dough was mixed at speed 1 for 30 seconds, followed by mixing at speed 2 for between about 4 and about 5 minutes. The two 100 g samples (A1 and A2 in FIGS. 3 and 4) and two 50 g samples (A3 and A4 in FIGS. 3 and 4) were placed in the Risograph testing machine used in connection with Example 1 above. The samples were incubated at about 30° C. for about 17 hours (1,000 minutes). The results of this Risograph testing are shown in FIGS. 3 and 4.

Figure 3:
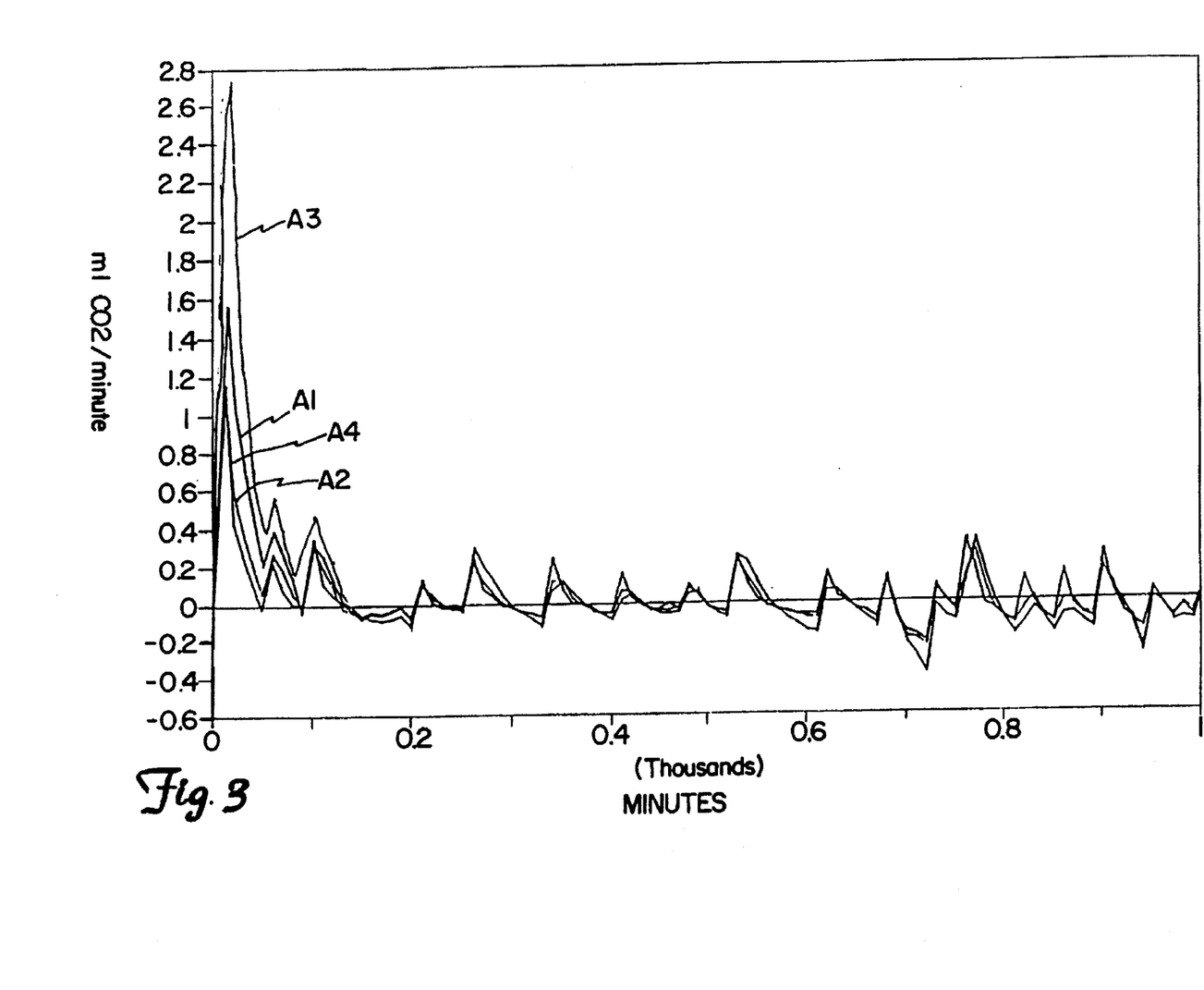
FIG. 3 is a graph depicting the rate of carbon dioxide generation over time for a GAL+ yeast in a dough composition held at 30° C.

As can be seen in FIG. 3, carbon dioxide was generated fairly rapidly in all of these samples for the first 40–50 minutes, after which the rate of evolution tapered off to about zero. Although the rate of carbon dioxide generation appears to have fluctuated between slight positive and negative rates, it appears as though the samples generated very little or no carbon dioxide between about 120 minutes after incubation began and the end of the experiment.

Figure 4:
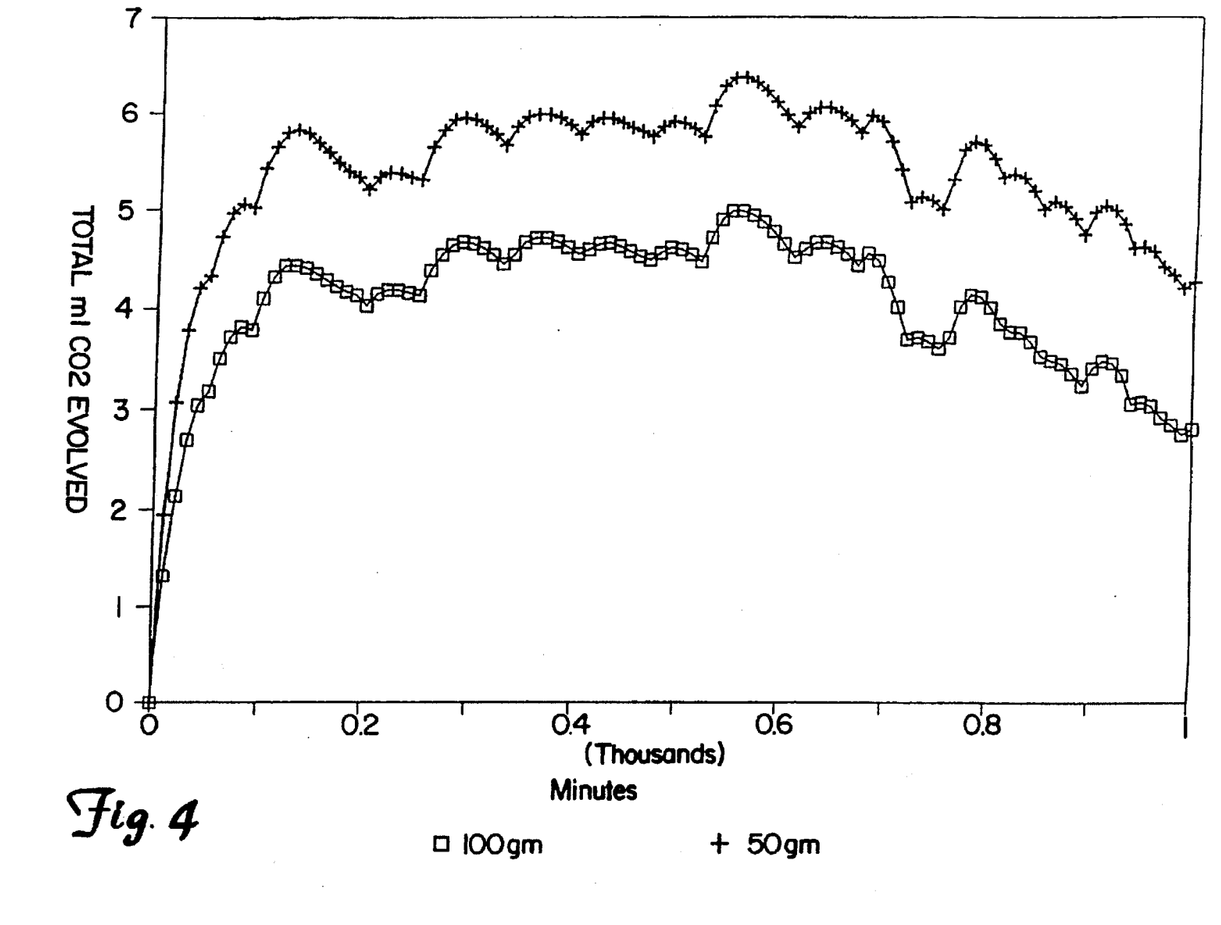
FIG. 4 shows the total volume of carbon dioxide generated in the sample of FIG. 3.

Furthermore, although the rate of carbon dioxide generation was noticeable at the beginning of the experiment, it should be noted that the total volume of carbon dioxide generated in this sample was no more than about 7 ml; this result is best seen in FIG. 4. As noted above, in order to adequately proof dough, between about 100 and about 200 ml of carbon dioxide/100 g of dough is generally considered to be necessary. The volume of carbon dioxide generated in these galactose-free samples, though, fell well below those limits. The indication that about 7 ml of gas was generated in these samples may actually be attributable primarily, if not entirely, to an expansion of the headspace in the Risograph sample containers when the containers were heated for incubation. In other words, it appears likely that no appreciable carbon dioxide was generated by the dough samples in this experiment.

Accordingly, the D308.3 yeast used in this Example can be said to be substantially incapable of fermenting, or otherwise metabolizing, the carbohydrates native to this dough system. Hence, it is believed that the D308.3 strain of yeast can be accurately referred to as GAL+, as that term is used herein, and this yeast provides one example of a yeast suitable for use in the present invention. As noted above, though, one of ordinary skill in the art could make other GAL+ yeasts, as well as other yeasts which are capable of fermenting only carbohydrates not native to the flour in the dough, in light of the present disclosure.

EXAMPLE 3

In order to test the responsiveness of the GAL+ yeast used in Example 2, four different dough compositions, with varying non-native carbohydrates, were prepared. Each of the four doughs included 290.25 g of flour, 176.60 g of water, 3.50 g of salt and 12.00 g of the D308.3 GAL+ yeast used in Example 1. The formulas of the four different doughs varied in the nature of the other ingredients which were added. In a control sample, no other ingredients were added; in a second sample, 5.00 g of galactose was included; in a third sample, 10.00 g of lactose was provided; and the final sample included 20.00 g of non-fat dry milk (NFDM), which is used a flavoring ingredient in some doughs and typically contains some lactose and may contain slight amounts of galactose.

Figure 5:
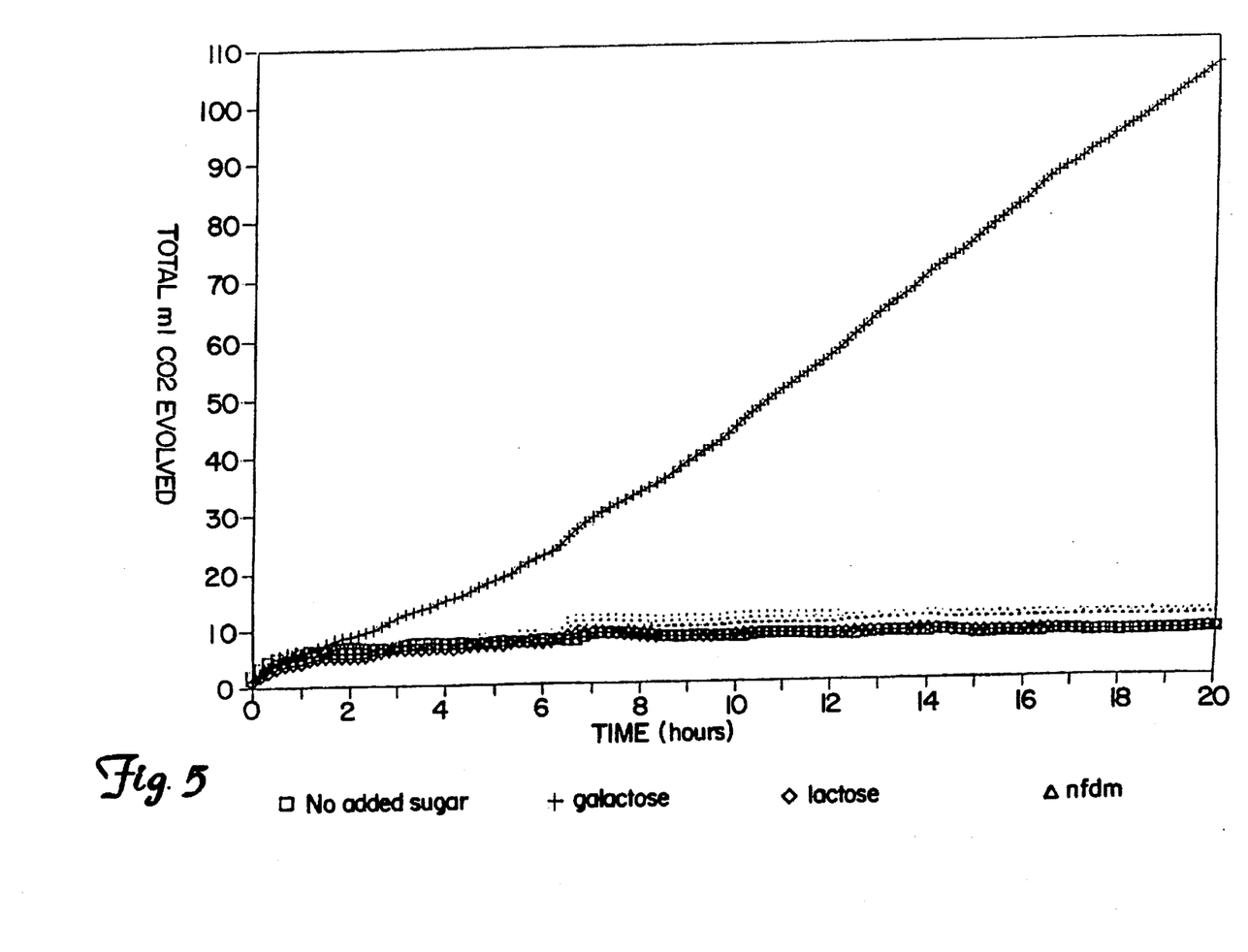
FIG. 5 is a graph showing the total volume of carbon dioxide generated by four dough compositions differing in the nature of non-native carbohydrates added to the dough.
Figure 6:
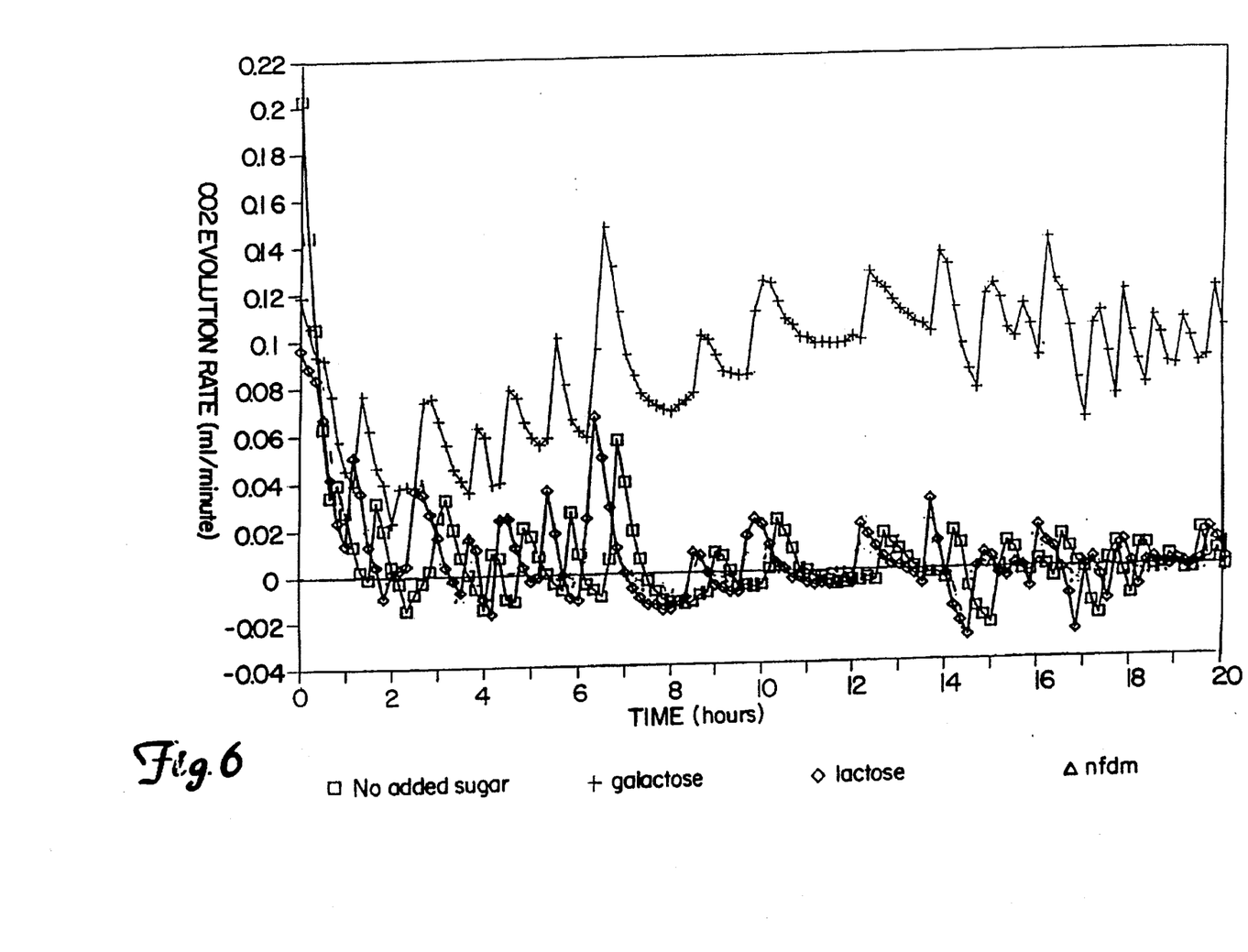
FIG. 6 is a depicts the rate of carbon dioxide evolution for the doughs shown in FIG. 5.

Yeast paste was grown and harvested in substantially the same manner as set forth in connection with Example 2. For each of the samples, the washed yeast was slurried with the water, and this slurry was added to the other ingredients in a table-top Hobart mixer. Each sample was then mixed at speed 1 for about 30 seconds, followed by mixing at speed 2 for about 4 minutes. Two 100 g samples of each of the dough compositions were placed into Risograph sample jars immediately after mixing and held in the Risograph at about 28° C. for approximately 20 hours. FIGS. 5 and 6 show the total volume of carbon dioxide evolved and the rate of carbon dioxide evolution, respectively, for each of the samples.

As can be seen from FIGS. 5 and 6, only the dough composition which included galactose generated appreciable volumes of carbon dioxide. The control sample, the lactose-containing sample and the sample with the NFDM all generated less than about 10 ml of carbon dioxide over a period of about 20 hours. Furthermore, essentially all of the carbon dioxide generation measured for the non-galactose doughs was generated in the first one to two hours of incubation. This slight change in gas volume in the Risograph sample jars may be wholly attributable due to thermal expansion of the headspace in the sample jars, as explained above. Accordingly, the samples which did not contain non-native galactose quite likely did not generate any significant amount of carbon dioxide during the course of this test.

The results of this experiment show that the D308.3 yeast can metabolize galactose but it is substantially incapable of fermenting any carbohydrates which are native to flour of the dough composition. It also appears that this yeast is substantially incapable of fermenting either "straight" lactose or lactose in non-fat dry milk. During the course of this experiment, the galactose-containing dough appears to continue to generate carbon dioxide, indicating that not all of the galactose was used. Furthermore, at the end of the 20-hour incubation, the galactose dough had generated slightly more than 100 ml of carbon dioxide, with carbon dioxide generation appearing to continue beyond the end of the experiment.

The dough containing galactose was about 1.0 wt. % galactose (5.00 g galactose/487.35 g total dough). Based on the results of this experiment, it appears that about 1 wt. % galactose is more than adequate to generate the desired 100–200 ml of carbon dioxide per 100 g of dough. Additional experimentation using standard, spirally wound composite containers of about 250 cc capacity, such as are commonly used in packaging commercial refrigerated doughs, has established that about 0.5 wt. % to about 1.0 wt. % galactose is sufficient to generate enough carbon dioxide to reach an internal pressure of about 10–20 psi. Accordingly, in making a refrigeratable dough product of the invention, the dough placed in the conger optimally includes between about 0.5 wt. % and about 1.0 wt. % galactose.

EXAMPLE 4

The D308.3 yeast was added to a chemically-leavened dough product in order to see if the presence of the GAL+ yeast affected the integrity of the container if no galactose was added to the dough. Two batches of a dough containing the D308.3 yeast and two separate batches of chemically leavened dough were prepared. The chemically leavened doughs had the following formula: about 1590 g (56 wt. %) flour, 947 g (33.43 wt. % water, 110 g (3.9 wt. %) of the wheat gluten pre-blend of Example 1, 89.2 g (3.15 wt. %) of yeast flavorings, 42.5 g (1.5 wt. %) glucono delta lactone (GDL), 32.0 g (1.13 wt. %) baking soda, and 21.3 g (0.75 wt. %) salt. The two batches of dough containing yeast had a very similar formula, with the approximately 947 g (33.4 wt. %) of water and yeast being replaced with about 890 g (31.4 wt. %) of water and about 56.7 g (2.00 wt. %) D308.3 yeast.

The water in each of these batches was first mixed with the flavoring ingredients before being charged with the flour and gluten pre-blend into a McDuffy mixing bowl. In the batches containing yeast, the yeast was slurried with the water before the flavoring ingredients were added to this slurry. The ingredients were mixed at speed 1 for about 30 seconds, followed by mixing at speed 2 for about 5 minutes. The salt and the leavening agents (GDL and soda) were then added to this dough and the mixture was mixed at speed 1 for approximately 30 seconds and at speed 2 for about 2.5 minutes.

Each batch of dough was sheeted to a thickness of about ¼ inch (about 0.64 cm) and rolled into a long "log" of dough. Each log of dough was divided into a series of samples weighing about 210 g and each sample was sealed into a standard, spirally wound composite can having a 250 cc capacity. These dough products were then proofed at about 32°–35° C. until an internal pressure of about 10–15 psi in the containers was reached. After this proofing, the dough products were transferred to refrigerated storage at about 4° C.

Figure 7:
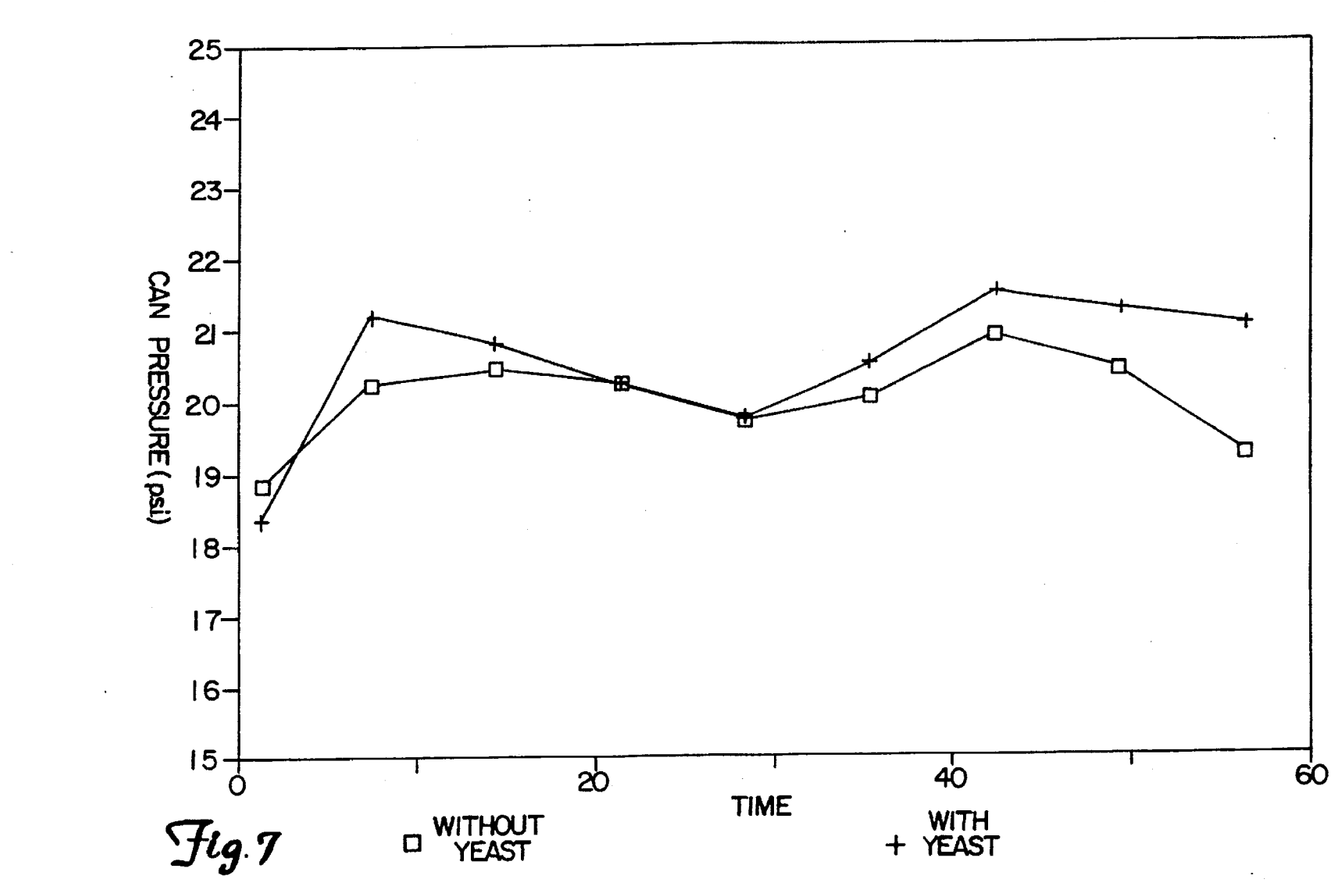
FIG. 7 plots measured can pressure over time for two chemically leavened doughs, one containing a GAL+ yeast, the other without.

FIG. 7 plots the measured can pressure, i.e., the internal pressure of the container, as a function of time. As can be seen in FIG. 7, there does not appear to be any significant difference between the pressure in the dough product containing the standard chemically leavened dough and the dough product containing the chemically leavened dough with the GAL+ yeast.

A variety of other physical measurements were made on the different samples to compare the standard chemically leavened dough with the yeast-doped dough. Among the physical measurements compared were water retention, pH, and sugar content. Samples of the doughs were also baked at approximately 375° F. (163° C.) for about 20 minutes. The specific volume, as well as the appearance, aroma and other sensory properties, of the resulting baked goods were compared. Aside from a slightly lower specific volume for the sample containing the GAL+ yeast, there did not appear to be any significant differences between these two dough compositions.

EXAMPLE 5

The relationship between galactose content of the dough and the resultant internal pressures of dough products containing dough in accordance with the invention was tested. Four different batches were prepared, with the batches differing only in the amount of galactose added. Each dough composition contained about 870.75 g (58.05 wt. %) wheat flour, 529.80 g (35.32 wt. %), water, 58.20 g (3.88 wt. %) of the wheat gluten preblend used in Example 1, 11.25 g (0.75 wt. %) salt and 28.50 g (2.00 wt. %) D308.3 yeast. Additionally, one batch contained about 5.92 g (0.5 wt. %) galactose, another contained about 7.40 g (0.63 wt. %) galactose, a third contained about 8.87 g (0.75 wt. %) galactose, and the final batch contained about 11.83 g (1.00 wt. %) galactose.

The D308.3 yeast was grown and harvested in substantially the same manner as that detailed above in Example 2. In forming batches of dough containing the 0.5 wt. % and 1.0 wt. % galactose, the yeast paste was then mixed with the water and the galactose in a 1 L culture flask and incubated in the flask for about 1 hour at about 30° C. while the flask was agitated. This slurry was then added to a McDuffy mixing bowl and mixed with the other ingredients at speed 1 for about 30 seconds, followed by mixing at speed 2 for about 7 minutes. The 0.63 wt. % and 0.75 wt. % galactose batches were prepared slightly differently in that they yeast, water and galactose were not incubated prior to being mixed with the other ingredients. Instead, these three ingredients were slurried in a table-top Hobart and were mixed at speed 2 for only about 4 minutes with a dough hook.

After the doughs were mixed, two 50-gram samples from each batch of dough were placed in Risograph sample jars and incubated in the Risograph at about 28°–30° C. The dough was then rolled, divided into 210-gram samples, and packaged in a standard refrigeratable dough container, as outlined above in Example 4. The resultant dough product was incubated at about 35° C. for about three hours and subsequently stored at about 4° C.

Figure 8:
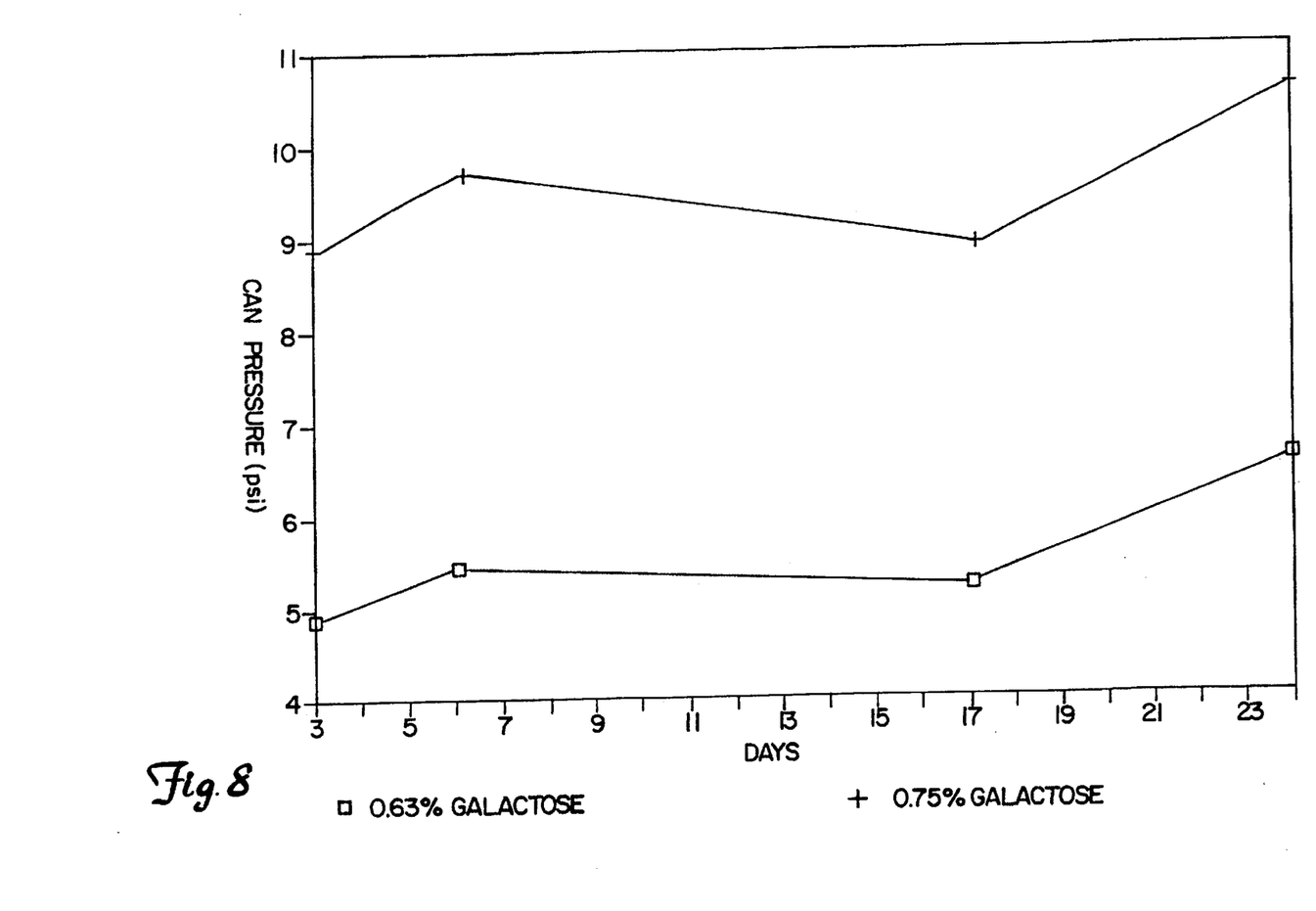
FIGS. 8 and 9 show can pressure over time for three dough samples having different amounts of non-native sugar incorporated in their composition.
Figure 9:
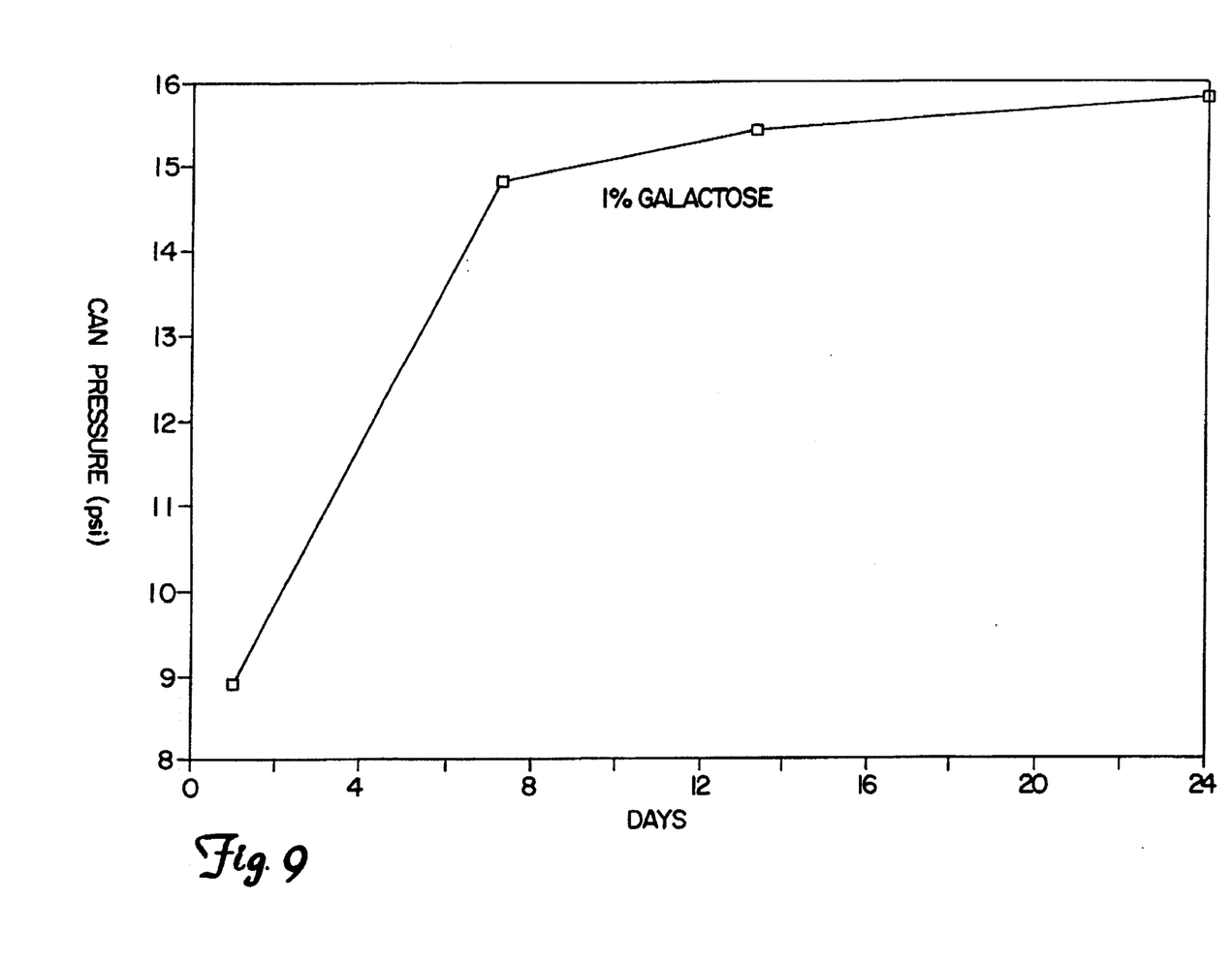

FIGS. 8 and 9 illustrate the can pressures of the samples in the Risograph as a function of time, with the can pressures for samples from each batch being averaged together to generate these plots. It can be seen that the ultimate can pressure of the sample is generally proportional to the mount of galactose in the dough. Whereas the sample containing 0.63 wt. % galactose had a can pressure of about 5–6.5 psi, the 0.75 wt. % dough had can pressures of about 9–10.5 and the pressure in the dough with 3 wt. % yeast and 1 wt. % galactose generated a maximum pressure of just under 16 psi. Accordingly, it appears as though the desired pressure in a container of the invention can be fairly readily controlled as a simple function of the mount of galactose added to the dough—once the galactose is exhausted, the dough will substantially cease producing carbon dioxide.

EXAMPLE 6

The D308.3 yeast perhaps adversely affected the sensory appeal of baked doughs containing such yeast in that the final baked product exhibited a slightly off-white color. Although all of the other organoleptic qualities of the dough were exemplary, doughs which would not exhibit this slight discoloration would probably be more appealing to consumers. It was determined that the discoloration of the dough was most likely due to inability of the D308.3 yeast to make adenine, causing the yeast to develop a pinkish or reddish hue when it is grown in a medium without adenine supplementation. This discoloration of the yeast is presumed attributable to a build up of metabolites which are toxic to the yeast (but not to humans).

Spontaneous revertant strains of the D308.3 yeast which do not require adenine for metabolization, referred to herein as RD308.3 yeast, were isolated. First, a concentrated paste of the D308.3 yeast was formed by spinning down the yeast in a rotor, as outlined in Example 2. This yeast paste was then diluted with a potassium phosphate monobasic buffer (about 43 mg $KH_2PO_4$ added to a liter of distilled water, with the Ph adjusted to about 7.2 with NaOH) and spread on an "adenine drop out" (ADO) medium, i.e. a medium which does not contain any supplemental adenine, at a concentration of about $1\times10^7$ colony forming units (CFU)/ml. The ADO medium contained, for each liter of distilled water, about: 6.7 g of bacto-yeast nitrogen base without amino acids, 20 g galactose, and 20 g of bacto-agar, 2 g of a "drop out mix" which contained alanine, aregenine, asparagine, aspartic acid, cysteine, glutamine, glutamic acid, glycine, histidine, inositol, isoleucine, leucine, lysine, methionine, para-aminobenzoic acid, phenylalanine, proline, serine, threonine, tryptophan, tyrosine, uracil, and valine. (Substantially the same formula is taught by Rose et al. in Appendix A of *Methods in Yeast Genetics, A Laboratory Course Manual* (1990), which is incorporated herein by reference, at pages 179–180, but that formula used glucose rather than galactose.)

These ADO plates were incubated at about 25° C. for approximately 4 days and colonies of the yeast which did not require adenine were isolated. Identifying these colonies was greatly simplified by the fact that the non-revertant strains tended to be pinkish or reddish in hue while the revertant colonies were whitish. The isolated yeast was then once again plated onto a fresh ADO medium and incubated under substantially the same conditions. Colonies of revertant strains of the yeast were once again isolated from any strains inadvertently carried over in the first isolation and the platting and incubation were repeated one final time. Although it is believed that one skilled in the art could readily make such a yeast in light of the present disclosure, this resulting strain of RD308.3 yeast has been deposited with the ATCC on Mar. 5, 1993, under number ATCC 74212 and this swain is available to the public from the ATCC.

Two samples were prepared, with one sample containing the original D308.3 yeast and the other containing the RD308.3 yeast. These samples were prepared by mixing an isolated colony (about one loop) of the desired yeast with about 5 ml of YEP/galactose (which contained about 10 g of bacto-yeast extract, 20 g of bacto-peptone, and about 20 g of galactose per 1 liter of distilled water) and incubating for about 12–15 hours at about 30° C. (The formula for the YEP/galactose medium is substantially the same as the YEP/glucose formula taught on page 177 of Appendix A of *Methods in Yeast Genetics*, noted above, except that the glucose in that formula was replaced with galactose in the present medium.) Titer results indicated a population of approximately $48\pm2\times10^5$ CFU/ml for each strain. For each of the resulting samples, about 100 µl of the sample was added to three separate 5 ml potions of media, with one medium comprising just YEP, another comprising YEP and glucose and the third comprising YEP and galactose.

Figure 10:
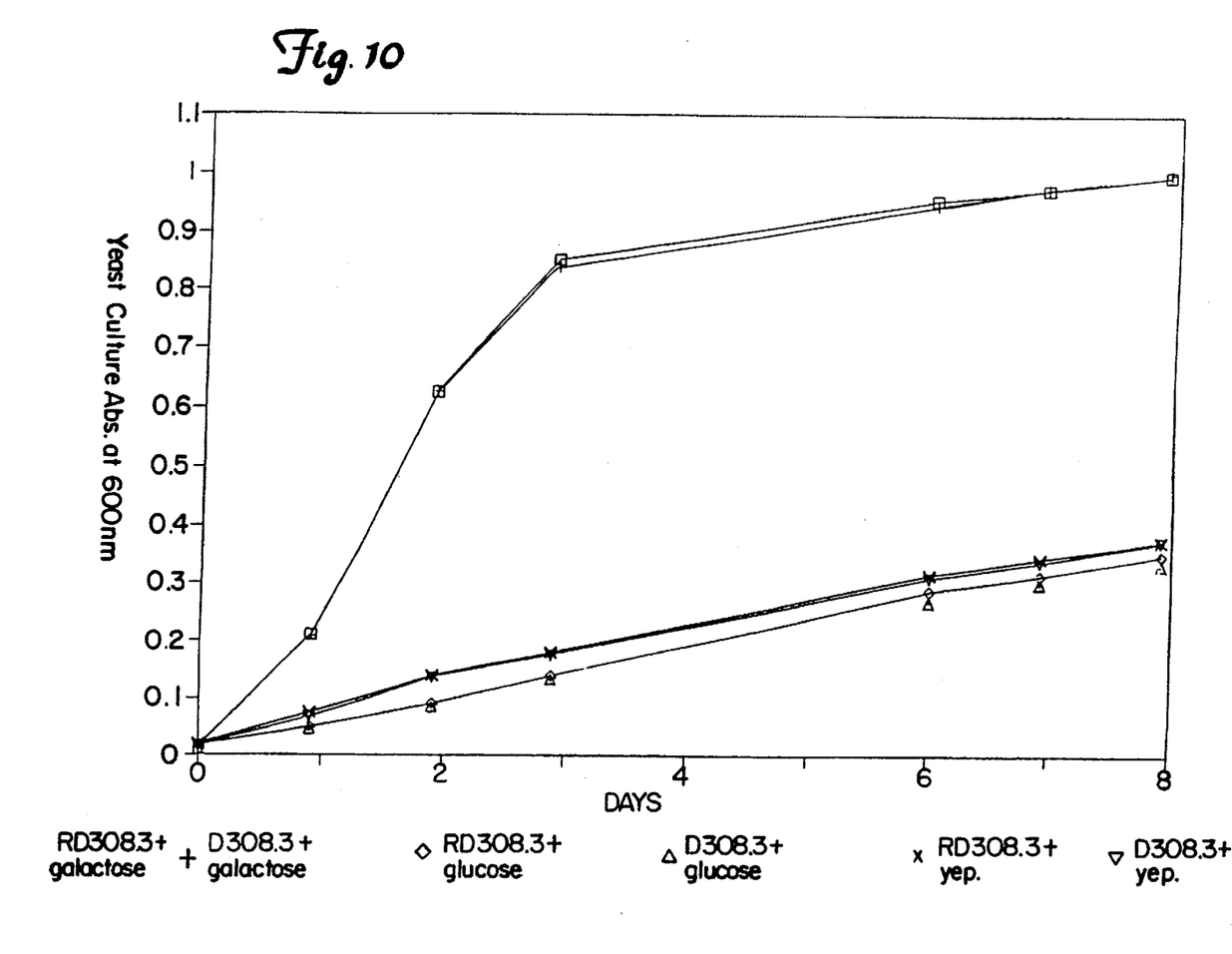
FIG. 10 depicts the growth of D308.3 and RD308.3 yeast on three different media as a function of absorbance.

The absorbance of each resulting sample was measured over time and is graphically illustrated in FIG. 10. The growth behavior of the D308.3 and RD308.3 yeasts appeared to be essentially the same for all three of these growth media. Furthermore, both of these yeasts appear able to readily metabolize galactose, but can only grow slightly on YEP or YEP/glucose. It is also interesting to note that both the D308.3 strain and the RD308.3 strain grew slightly less on the YEP/glucose than on YEP alone. This further demonstrates the substantial inability of these yeasts to metabolize glucose.

The auxotrophic markers adenine, histidine, methionine and tryptophan as growth supplements for the D308.3 and RD 308.3 strains were compared by standard techniques. The D308.3 yeast was not able to grow on galactose minimal media unless all four of these growth supplements were present, but the RD 308.3 yeast was able to grow if only the histidine, methionine and tryptophan were added.

Thus, the only significant difference noted between the auxotrophic markers of these two strains was that the D308.3 yeast requires adenine supplementation while the RD308.3 yeast does not. Accordingly, it is believed that the RD308.3 yeast will behave substantially as described above in connection with the D308.3 yeast when added to dough, but the slight discoloration of baked goods associated with doughs containing the D308.3 yeast should be substantially eliminated.

Another embodiment of the present invention provides a method of forming a dough which can be stored at refrigeration temperatures for extended periods of time without generating significant volumes of carbon dioxide. This method may further include the steps of packaging the dough, proofing the dough in the package, and storing the dough for an extended period of time at refrigeration temperatures.

In making a dough of the invention, flour, water, a yeast substantially incapable of fermenting carbohydrates native to the flour, and a quantity of a carbohydrate fermentable by the yeast are mixed together, as outlined above. The mount of the fermentable carbohydrate added to the dough is desirably sufficient to provide only the necessary degree of proofing of the dough; adding too much fermentable substrate could cause adverse changes in dough rheology due to overfermentation. This mount is optimally determined on a case-by-case basis for a given strain of yeast as different strains of yeast may utilize the fermentable substrate more efficiently than others.

In a particularly preferred embodiment of the method of the invention, the yeast used in making the dough is a GAL+ yeast and a predetermined quantity of galactose is added to the dough to provide the desired degree of proofing. This GAL+ may be the D308.3 yeast or the RD308.3 yeast described above, but it is to be understood that other GAL+ yeasts can be made in accordance with the present disclosure which will also work in accordance with the invention.

As noted above, the method may further include the steps of packaging the dough, proofing the dough in the container, and storing the dough at refrigeration temperatures for an extended period of time. Virtually any known refrigeratable dough package known in the art may be used in this method. For instance, spirally wound dough containers such as those currently used in commercially manufactured refrigeratable dough products should suffice. A quantity of dough somewhat less than that necessary to fill the container is placed in the container, leaving a headspace in the container when it is sealed.

The dough may then be proofed in the container, expanding to fall the container and flush out any air in the headspace. The proofing is continued until substantially all of the fermentable carbohydrate is consumed by the yeast, at which point an internal pressure of about 15 to about 20 psi is attained in the container. This proofing may be advantageously carried out at an elevated temperature, e.g. about 30° C. to about 40° C., to allow the yeast to ferment, and thus proof the dough, more rapidly.

This proofed dough may then be placed in refrigerated storage for extended periods of time, desirably up to at least about two weeks. The dough of the invention is optimally capable of storage at refrigeration temperatures for at least about 90 days, the anticipated shelf life of current doughs, as explained above. By "refrigerated storage", storage at temperatures between about 12° C. and about 0° C., and preferably between about 4° and bout 7.2° C., is intended. Such temperatures are referred to in the present specification as "refrigeration temperatures".

While preferred embodiments of the present invention have been described, it should be understood that various changes, adaptations and modifications may be made therein without departing from the spirit of the invention and the scope of the appended claims.

What is claimed is:

1. A method for making a refrigeratable dough product comprising mixing *Saccharomyces cerevisiae* ATCC 74212, with wheat flour, a carbohydrate other than wheat flour containing galactose fermentable by said *Saccharomyces cerevisiae* and water, and preparing said dough.

* * * * *

UNITED STATES PATENT AND TRADEMARK OFFICE
CERTIFICATE OF CORRECTION

PATENT NO. : 5,650,183
DATED : July 22, 1997
INVENTOR(S) : David J. Domingues

It is certified that error appears in the above-indentified patent and that said Letters Patent is hereby corrected as shown below:

On title page,

Related U.S. Application Data, delete "Jul. 28, 1994" and insert --Jul. 20, 1994--.

Column 1, line 9, after "Ser. No. 07/732,081," insert --filed July 18, 1991--.

Column 1, line 62, delete the word "theological" and insert the word --rheological--.

Column 3, line 50, after the words "FIG. 6" delete the words --is a--.

Column 4, line 53, please delete the word "swain" and insert the word --strain--.

Column 4, line 56, please delete the word "mutes" and insert the word --minutes--.

Column 4, line 65, please delete the number "1.130" and insert the number --1.00--.

Column 5, line 55, please delete the word "ease" and insert the word --case--.

Column 6, line 22, please delete the word "mount" and insert the word --amount--.

Column 6, line 27, after the word "weight", please delete the word "to".

Column 6, line 30, please delete the word "mount" and insert the word --amount--.

Column 6, line 32, please delete the word "mount" and insert the word --amount--.

Column 9, line 30, please delete the word "conger" and insert the word --container--.

Column 9, line 42, after the word "(33.43 wt. %" insert the right parenthesis --)--.

Column 10, line 50, delete the word "they" and insert the word --the--.

Column 10, line 67, please delete the word "mount" and insert the word --amount--.

Column 11, line 8, please delete the word "mount" and insert the word --amount--.

Column 11, line 65, please delete the word "swain" and insert the word --strain--.

UNITED STATES PATENT AND TRADEMARK OFFICE
CERTIFICATE OF CORRECTION

PATENT NO. : 5,650,183
DATED : July 22, 1997
INVENTOR(S) : David J. Domingues

It is certified that error appears in the above-indentified patent and that said Letters Patent is hereby corrected as shown below:

Column 12, line 14, please delete the word "potions" and insert the word --portions--.

Column 12, line 56, please delete the word "mount" and insert the word --amount--.

Column 12, line 61, please delete the word "mount" and insert the word --amount--.

Column 13, line 18, please delete the word "fall" and insert the word --fill--.

Column 14, line 9, please delete the word "bout" and insert the word --about--.

Signed and Sealed this

Third Day of November, 1998

BRUCE LEHMAN

*Attest:*

*Attesting Officer*

*Commissioner of Patents and Trademarks*